(12) United States Patent
Cheng et al.

(10) Patent No.: US 10,301,334 B1
(45) Date of Patent: May 28, 2019

(54) METHOD FOR PREPARING STABILIZER CONTAINING PHOSPHATE-ESTER

(71) Applicant: Far Eastern New Century Corporation, Taipei (TW)

(72) Inventors: Hsin-Hui Cheng, Taipei (TW); Cheng-Ting Wang, Taipei (TW); Der-Ren Hwang, Taipei (TW); Chih-Chien Lin, Taipei (TW)

(73) Assignee: Far Eastern New Century Corporation, Taipei (TW)

( * ) Notice: Subject to any disclaimer, the term of this patent is extended or adjusted under 35 U.S.C. 154(b) by 0 days.

(21) Appl. No.: 16/016,693

(22) Filed: Jun. 25, 2018

(30) Foreign Application Priority Data

Feb. 14, 2018 (TW) .............................. 107105506 A

(51) Int. Cl.
*C07F 9/09* (2006.01)
(52) U.S. Cl.
CPC ....................................... *C07F 9/09* (2013.01)
(58) Field of Classification Search
CPC ....................................................... C07F 9/09
See application file for complete search history.

(56) References Cited

U.S. PATENT DOCUMENTS

| 3,663,600 A | * | 5/1972 | McConnell et al. .... C07C 67/60 |
| | | | 560/78 |
| 4,110,316 A | | 8/1978 | Edging |
| 4,122,063 A | | 10/1978 | Alexander |
| 6,384,180 B1 | | 5/2002 | Jernigan |

FOREIGN PATENT DOCUMENTS

| CN | 1174556 | 2/1998 |
| CN | 102911203 | 2/2013 |
| CN | 103833785 | 6/2014 |
| JP | S48-23808 | 7/1973 |
| JP | 2018-109134 A | 7/2018 |

\* cited by examiner

*Primary Examiner* — Yevgeny Valenrod
*Assistant Examiner* — Blaine G Doletski
(74) *Attorney, Agent, or Firm* — Winston Hsu

(57) ABSTRACT

A method for preparing a stabilizer containing phosphate ester, including following steps: (1) distributing a compound containing phosphorous and oxide in polar aprotic solvent to obtain a mixture; (2) adding bis(2-hydroxyethyl) terephthalate (BHET) into the mixture to carry out a reaction so as to obtain a solution; and (3) hydrolyzing the solution to obtain a stabilizer containing phosphate ester, where the stabilizer includes compounds represented by the following formulas (I) and (II):

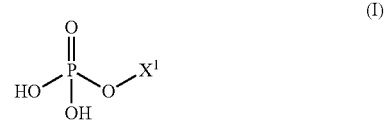

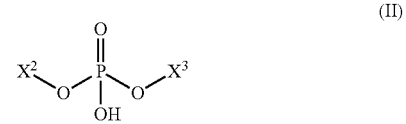

where $X^1$, $X^2$ and $X^3$ are independently selected from the moiety represented by following formula (III), and $R^1$ and $R^2$ are independently selected from one of the linear or branched alkylene radicals comprising 2 to 4 carbon atoms

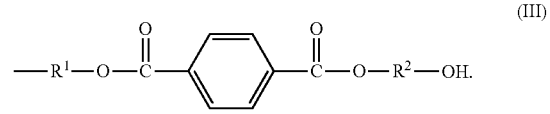

The method yields a phosphate ester containing a phosphate monoester and a phosphate diester of a high content and only a minor amount of phosphoric acid in the absence of phosphate triester without the step of extraction.

9 Claims, 3 Drawing Sheets

METHOD FOR PREPARING STABILIZER CONTAINING PHOSPHATE-ESTER

BACKGROUND OF THE INVENTION

1. Field of the Invention

The present invention relates generally to a method for the preparation of a stabilizer containing phosphate ester, and more particularly to a method for the preparation of a stabilizer containing phosphate ester for use in the addition in a condensation polymerization reaction of a polyester resin.

2. Description of the Prior Art

The polyester resin is a polymer prepared by a condensation polymerization. Generally speaking, in order to accelerate the reaction rate of the condensation polymerization reaction, a metal catalyst is added to the reaction solution to accelerate the progress of the condensation polymerization reaction. The above-mentioned metal catalyst may include a metal such as antimony, titanium, or germanium or their complex compounds. However, although these metal catalysts can accelerate the polymerization reaction, they also cause a degradation reaction of the polymerized polyester resin at the same time during the polymerization reaction so that the resultant products may have a poor hue or a decreased molecular weight. To solve the above problems, the industry usually further adds a stabilizer into the reaction solution to reduce the activity of the catalyst. So far the most frequently used stabilizers are mostly phosphorus-containing stabilizers, such as phosphoric acid, phosphorous acid or their derivatives.

However, when the phosphorus-containing stabilizers are used, other problems may arise accordingly. For example, the stabilizers may excessively reduce the activity of the catalyst to result in an excessive increase of the reaction time of the polymerization. In addition, the correspondingly obtained polyester resins generally have worse heat resistance so the viscosity of the polyester resin is significantly reduced during a secondary processing stage to adversely influence the subsequent processing of the polyester resin.

In view of these drawbacks, it is still necessary to propose an improved stabilizer that not only does it not cause the reaction time of the polymerization reaction to be excessively prolonged but the heat resistance of the correspondingly obtained polyester resin is also increased.

SUMMARY OF THE INVENTION

According to one embodiment of the present invention, a method for the preparation of a stabilizer containing phosphate ester is provided. The method includes at least the following steps:
(1) A phosphorous oxide compound is dispersed in a polar aprotic solvent to obtain a mixture. In particular, there is no chemical reaction between the phosphorus oxide compound and the polar aprotic solvent, and the polar aprotic solvent act as a proton acceptor.
(2) Next, bis(2-hydroxyethyl) terephthalate (BHET) is added into the mixture to carry out a phosphorylation reaction so as to obtain a reaction solution. In particular, the bis(2-hydroxyethyl) terephthalate (BHET) has a melting point between 105° C. and 115° C.
(3) Then, the reaction solution is hydrolyzed to obtain the stabilizer which includes phosphate ester. The stabilizer includes the phosphate ester structures represented by the following formula (I) and formula (II) and some minor phosphoric acid but is free from a phosphate triester:

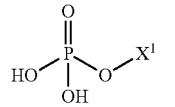

(I)

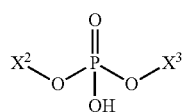

(II)

wherein $X^1$, $X^2$ and $X^3$ are independently selected from the moiety represented by the following formula (III):

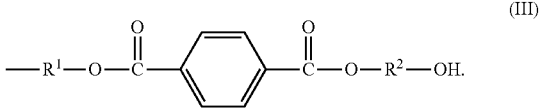

(III)

with 1 or 2 repeating units in the molecular chain, and $R^1$ and $R^2$ are independently selected from one of a linear alkylene group containing 2 to 4 carbon atoms and a branched alkylene group containing 3 to 4 carbon atoms in total.

According to the above embodiments, a method for the preparation of a stabilizer including a phosphate ester is provided to yield a phosphoric acid monoester of a high content and a phosphoric acid diester of a high content without the need of extraction, in the absence of any phosphoric acid triesters, and only a minor amount of phosphoric acid is present. Preferably, a molar ratio between the phosphate ester and the phosphoric acid in the stabilizer is greater than 4. Compared with the conventional stabilizers of phosphoric acid for use in a polymerization reaction, the resultant polyester resins which are obtained by using the stabilizer of the present invention may maintain better heat resistance so the viscosity of the polyester resins is not significantly reduced during a secondary processing stage to favor the subsequent processing of the polyester resins.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
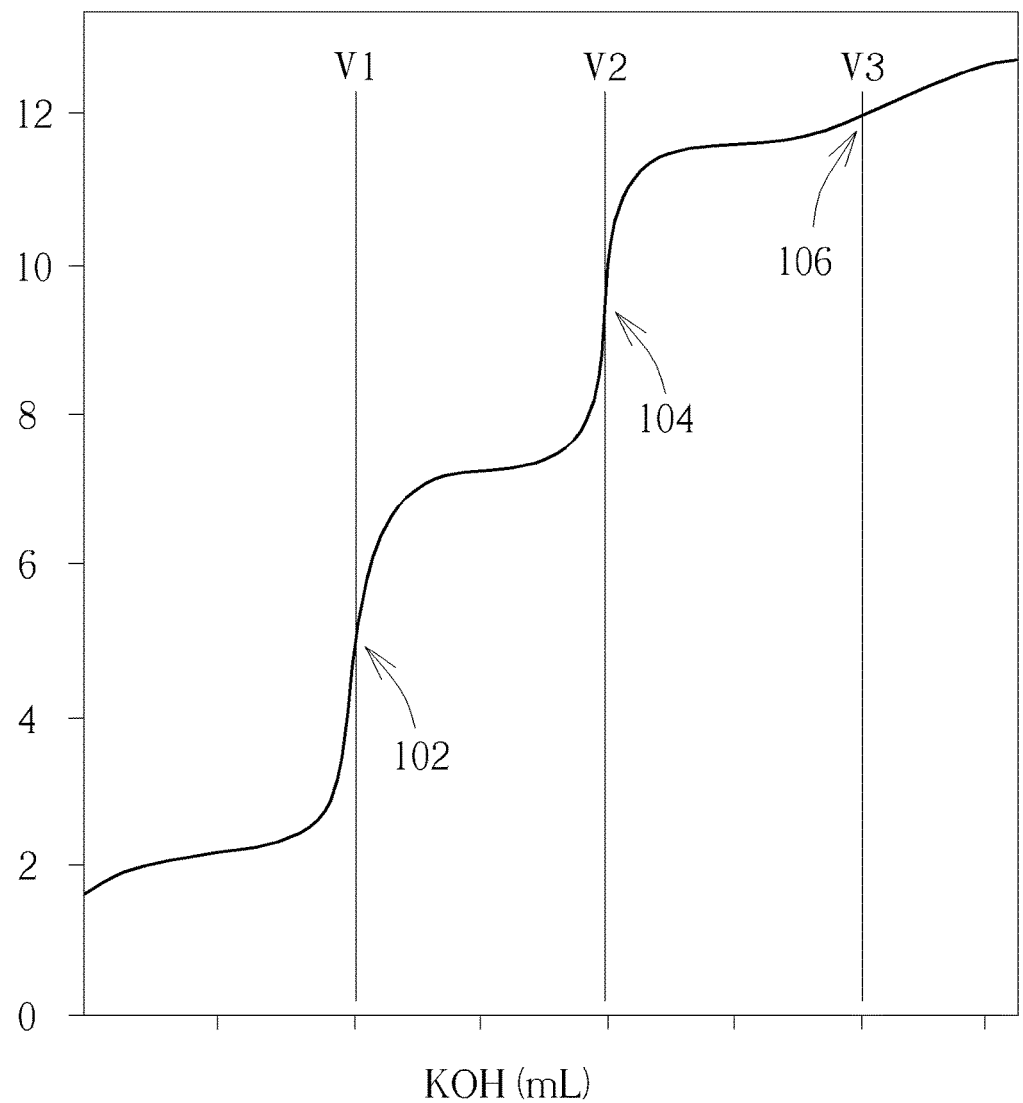
FIG. 1 is graph to illustrate the titration of phosphoric acid esters with potassium hydroxide according to one embodiment of the present invention.

In the following paragraphs, in order to describe a specific range of values, the expression 'a value to another value' is used, and it should be interpreted as covering any numerical value within the range of values and a smaller range defined by any numerical value within the numerical range as the written values and the smaller numerical range recited in the specification. In addition, for the sake of simplicity and brevity, some structures of the respective polymers or moieties hereinafter are sometimes represented by a 'skeleton formula' to omit the carbon atoms, hydrogen atoms and carbon-hydrogen bonds within the actual structure. However, where a specific atom or a moiety is explicitly shown in a structural formula, the structural formula should be taken as a reference.

According to one embodiment of the present invention, a method for the preparation of a stabilizer including a phosphate ester is provided. The method includes at least the following steps. First, a phosphorus oxide compound or its derivative is dispersed in a polar aprotic solvent to form a mixture solution.

The above-mentioned phosphorus oxide compound may be selected from at least one of phosphoric acid ($H_3PO_4$), polyphosphoric acid (PPA), phosphorous pentoxide ($P_2O_5$), or any combination thereof, and is preferably phosphorus pentoxide.

The polar aprotic solvent is a polar solvent of high polarity to serve as a proton acceptor, and it additionally should have the following characteristics: good solubility with the reactants, no chemical reactions with the phosphorus oxide compounds, and a boiling point higher than the reaction temperature of the phosphorylation reaction (the reaction temperature of the phosphorylation reaction is generally between 60° C.-90° C.). Preferably speaking, the polar aprotic solvent is selected from cyclic carbonates, such as ethylene carbonate and propylene carbonate, but they are not limited thereto.

Next, the compounds which are represented by the following formula (IV) are added to the above-mentioned mixture solution. The compounds have terminal hydroxyl groups to serve as a proton donor, so they are readily able to be well dispersed in the above-mentioned polar solvent of high polarity with the ability of serving as a proton acceptor. $R^1$ and $R^2$ in the formula (IV) are independently selected from one of a linear alkylene group containing 2 to 4 carbon atoms and a branched alkylene group containing 3 to 4 carbon atoms in total. Preferably speaking, a molar ratio of the phosphorus oxide compounds and the compounds represented by the formula (IV) in the mixture solution is between 1:1 and 1:2, and more preferably is between 1:1.1 and 1:1.5.

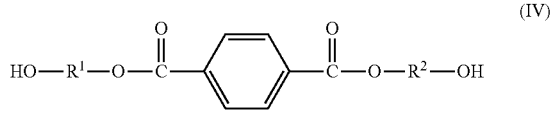

(IV)

Preferably speaking, the compound represented by the above formula (IV) is bis(2-hydroxyethyl) terephthalate (BHET), with 1 or 2 repeating units in the molecular chain. It is in a form of a monomer with a melting point approximately between 105° C. and 115° C., and preferably between 106° C. and 110° C. For example, it may be selected from the commercially available reagent grade chemical (CAS NO.: 959-26-2), from a product which is obtained from the alcoholysis of polyethylene terephthalate (PET) by ethylene glycol, or from a product which is obtained from the reaction of terephthalic acid (TPA) with ethylene oxide, or from a product which is obtained from the polymerization of terephthalic acid with ethylene glycol. However, in the case where BHET is obtained from the esterification polymerization of terephthalic acid and ethylene glycol, it is not suitable for use in the preparation method of the present invention because most of the BHET molecules which are obtained from this reaction are oligomers with 3 to 10 repeating units in the molecular chain. Accordingly it is not suitable to serve as the raw material of bis(2-hydroxyethyl) terephthalate for use in the preparation method of the present invention.

Next, the temperature of the mixture solution in the reaction flask rises to a range between 75° C. and 85° C. in the form of gradual rise, and the temperature is maintained for 2 to 4 hours to carry out a phosphorylation reaction to obtain a reaction solution. The reaction solution includes phosphate esters, i.e. phosphoric acid esters, which are represented by the following formulas (I), (II) and (V):

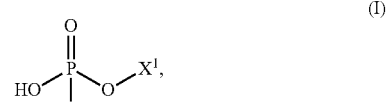

(I)

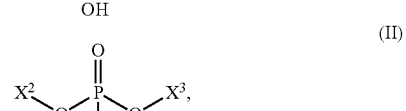

(II)

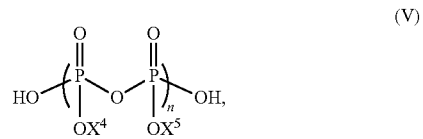

(V)

wherein $X^1$, $X^2$, $X^3$, $X^4$ and $X^5$ are independently selected from the moiety represented by the following formula (III) with 1 or 2 repeating units in the molecular chain of the moiety and n is an integer between 1 and 3 in the above-mentioned formula (V):

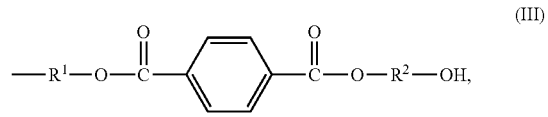

(III)

and $R^1$ and $R^2$ are independently selected from one of a linear alkylene group containing 2 to 4 carbon atoms and a branched alkylene group containing 3 to 4 carbon atoms in total.

At last, based on the total weight of the initial phosphorus oxide compounds and the compounds represented by the formula (IV), deionized water of 1 wt. % to 3 wt. % content is added to the reaction flask at the temperature range 65° C.-75° C. maintained for 1 to 2 hours to carry out the hydrolysis reaction to obtain phosphoric acid ester compounds. The phosphoric acid ester compounds include the phosphoric acid esters represented by the above formula (I) and formula (II), and additionally include a phosphoric acid ester represented by the following formula (VI) and a minor amount of phosphoric acid. Further, there are 80 mol % to 89 mol % of the phosphoric acid esters and 20 mol % to 11 mol % of phosphoric acid (unreacted material), based on the total amount of phosphoric acid ester and phosphoric acid in the phosphoric acid ester compounds as 100 mol %.

In addition, the proportion of phosphoric acid (unreacted phosphoric acid) in the phosphoric acid ester compounds (the phosphoric acid esters together with phosphoric acid) is 20 mol % or less, preferably 11 mol %, and in particular the phosphoric acid ester compounds are free from a phosphoric acid triester.

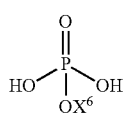

(VI)

The phosphoric acid esters which are represented by the formula (VI) are obtained from the hydrolysis of a phosphoric acid ester which is represented by the above formula (V), and $X^6$ is selected from the group represented in the above formula (III).

In accordance with the above embodiments, a method for the preparation of a stabilizer including a phosphate ester is provided. One of the characteristics of the method lies in that the composition of the stabilizer includes a phosphoric acid monoester and a phosphoric acid diester, and the major structure is the phosphoric acid monoester structure. The chemical structure of the phosphoric acid monoester is represented by the above formula (I) and by the above formula (VI).

In addition, the stabilizer which is prepared by the above method only has a minor amount of phosphoric acid. Specifically speaking, the phosphoric acid content in the stabilizer of the present invention may be less than 20 mol %.

In addition, another characteristic of the above-described preparation method is that a major amount of a phosphoric acid monoester along with a minor amount of phosphoric acid can be obtained without the need of extraction.

Therefore, when the above-mentioned stabilizer is added to a polymerization reaction of a polyester resin, not only does the degradation reaction rate of the polyester resins slow down in the polymerization process but the correspondingly obtained polyester resins also maintain better heat resistance because the stabilizer of the present invention is mainly composed of a phosphoric acid monoester and a phosphoric acid diester to be compared with the conventional stabilizer in which merely uses phosphoric acid in the polymerization reaction so the viscosity of the resultant polyester resins does not drop significantly in a secondary processing stage to favor the subsequent processing of the polyester resins.

In order to make one of ordinary skill in the art enable the practice of the present invention, various examples of the present invention will be further elaborated in details in the following paragraphs. It should be noted that the following examples are for illustrative purposes only and should not be construed to limit the present invention. That is, a material, the amount of a material and a ratio as well as a processing flow in the respective examples may be appropriately modified without exceeding the scope of the present invention.

The following is information of a list of abbreviation for each chemical material used in the following examples as well as its source:
Ethylene carbonate: purchased from Oriental Union Chemical Corporation (OUCC).
Phosphorus pentoxide: purchased from Showa Chemical Industry Co., Ltd.
BHET: Bis(2-hydroxyethyl) terephthalate, CAS NO.: 959-26-2, melting point 106° C.-110° C., B3429, purchased from Tokyo Chemical Industry Co.

Example 1

52.33 g of ethylene carbonate was added to a reaction flask followed by the addition of 14.19 g (0.10 mole) of phosphorus pentoxide ($P_2O_5$) in an ice bath. During the addition, the solution is continuously stirred so that phosphorus pentoxide can be uniformly dispersed in ethylene carbonate. Afterwards, a total weight of 38.14 g (0.15 mole) of BHET was stepwisely added to the above solution and continuously stirred. Then, the temperature of the reaction solution in the reaction flask was gradually raised to 80° C. and the temperature was maintained for 3 hours so that BHET and phosphorus pentoxide were subjected to the phosphorylation reaction. Next, 2 wt. % of deionized water, based on the total weight of the initial BHET and phosphorus pentoxide, was added to the reaction flask and the temperature was maintained at 70° C. for 1 hour to undergo the hydrolysis reaction. At last, the above phosphorylation reaction was terminated. After the ethylene carbonate component was removed, a batch of compounds of phosphoric acid and esters of 52.33 g was obtained. These compounds of phosphoric acid and esters may be used as a stabilizer including phosphate esters (A-1). Subsequently, 0.55 g of the compounds of phosphoric acid and esters were taken out to be dissolved in a solvent consisting of 75 g of distilled water and 25 g of isopropanol. The pH value was 2.27 when it was measured with a pH meter (Model: Seven Multi™, Mettler Toledo).

The above-mentioned compounds of phosphoric acid and esters include a phosphoric acid monoester, a phosphoric acid diester and phosphoric acid. Subsequently, the above-mentioned compounds of phosphoric acid and esters may be further titrated with a 0.1 M aqueous potassium hydroxide solution to confirm the respective proportion of the phosphoric acid monoester, the phosphoric acid diester and phosphoric acid.

Referring to the titration curve of FIG. 1, during the titration a first titration endpoint 102, a second titration endpoint 104, and a third titration endpoint 106 may be sequentially obtained. They may respectively correspond to the titration volumes V1, V2 and V3 of potassium hydroxide. The contents of the phosphoric acid monoester, the phosphoric acid diester and phosphoric acid in the compounds of phosphoric acid and esters can be calculated according to the following Formula I, Formula II, and Formula III. The calculated results are shown in Table 1 below.

The molar ratio of the phosphoric acid monoester (mol %)=$(2V_2-V_1-V_3)/V_1*100\%$   Formula I The molar ratio of the phosphoric acid diester (mol %)=$(2V_1-V_2)/V_1*100\%$   Formula II The molar ratio of phosphoric acid (mol %)=$(V_3-V_2)/V_1*100\%$   Formula III In order to confirm the species of the phosphoric acid monoesters and the phosphoric acid diesters, the electrospray ionization mass spectrometer (ESI-MS) (EVOQ™-Impact™ HD, Bruker), and a $^{31}P$ nuclear magnetic resonance instrument ($^{31}P$ NMR from Bruker at 400 MHz with DMSO as the solvent) were further used to analyze the above compounds of phosphoric acid and esters. The internal standard for 0 ppm was $H_3PO_4$.

Figure 2:
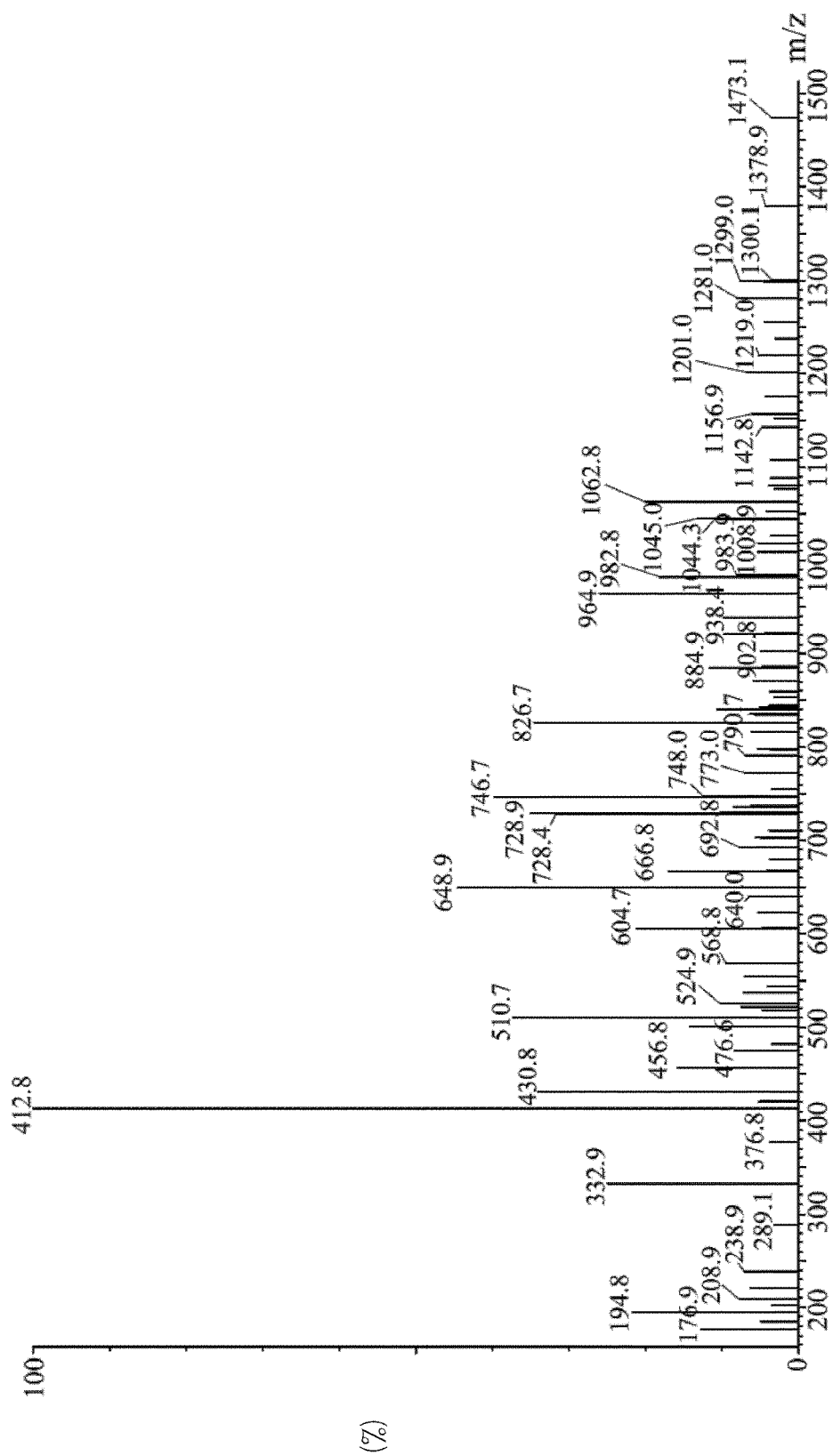
FIG. 2 is a mass spectrum for the analysis of phosphoric acid esters by using an electrospray ionization mass spectrometer according to one embodiment of the present invention.

The test results of the above ESI-MS analysis are shown in FIG. 2. According to the spectra shown in FIG. 2, it can be confirmed that the phosphoric acid monoester in the compounds of phosphoric acid and esters has a structure shown in the following formula (VII) based on the signal of mass-to-charge ratio (m/z) of 332.9, and the phosphoric acid diester in the compounds of phosphoric acid and esters has a structure shown in the following formula (VIII) based on the signal of mass-to-charge ratio (m/z) of 568.8:

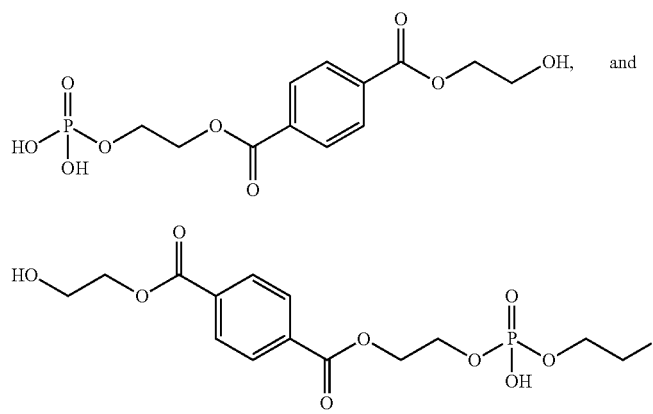

Figure 3:
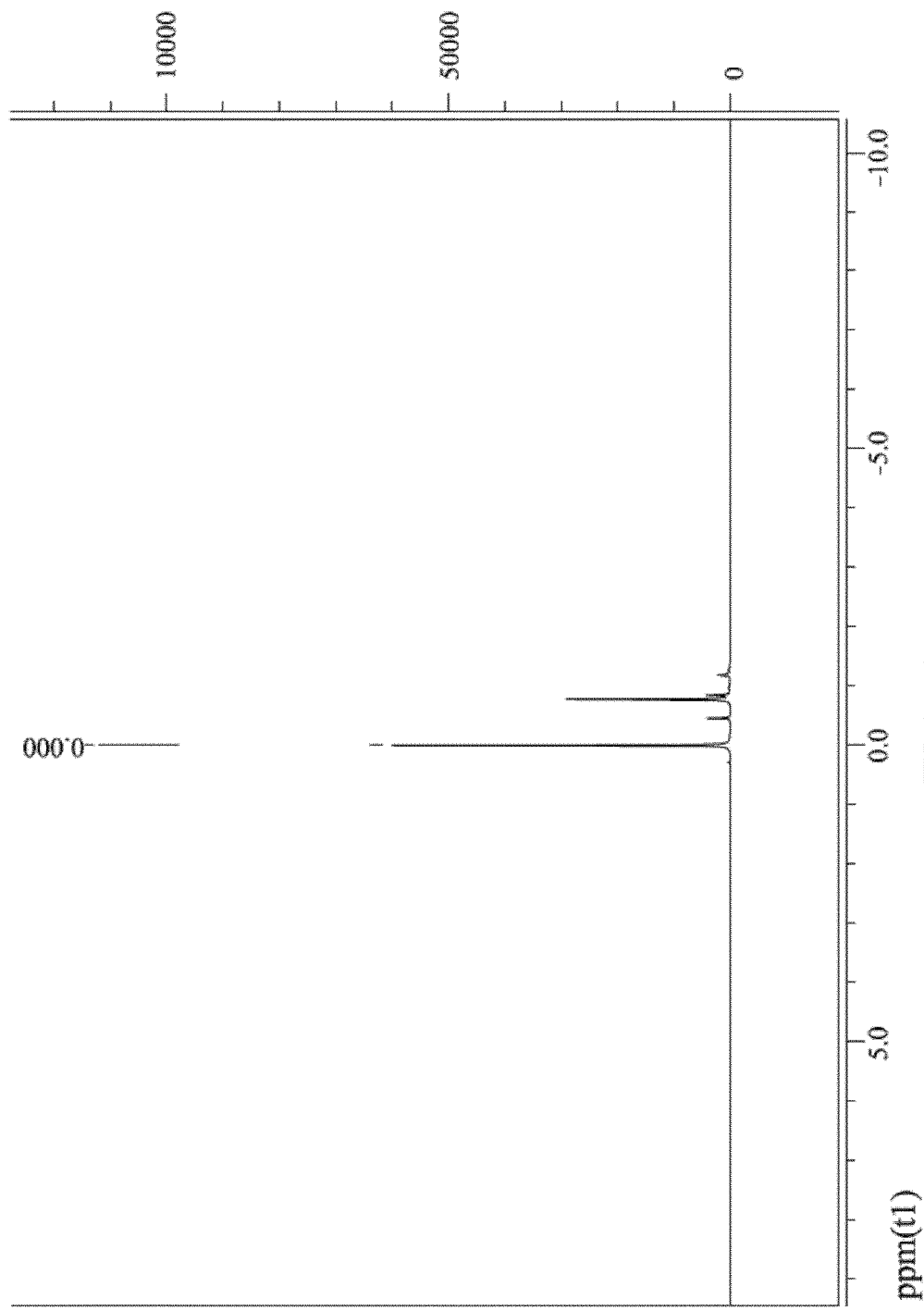
FIG. 3 is a $^{31}P$ nuclear magnetic resonance ($^{31}P$ NMR) spectrum for the analysis of the phosphoric acid esters by a $^{31}P$ nuclear magnetic resonance instrument according to one embodiment of the present invention.

In addition, the test results of $^{31}P$ NMR are shown in FIG. 3. According to the spectra shown in FIG. 3, it can also be confirmed that the phosphoric acid monoester and the phosphoric acid diester in the compounds of phosphoric acid and esters respectively have the formula (VII) and the formula (VIII) as described above according to the the signal peaks of the chemical shift of δ=0 to −2 ppm. A pyrophosphate ester or a polyphosphate ester is confirmed to be absent from the compounds of phosphoric acid and esters.

Example 2

The manufacturing procedures in Example 2 were substantially the same as the manufacturing procedures in Example 1 except that 40.56 g of ethylene carbonate was used and the total amount of BHET was 26.37 g (0.10 mole) in Example 2 instead. After the phosphorylation reaction and the hydrolysis reaction and after the removal of the ethylene carbonate component, a total weight of 40 g of the compounds of phosphoric acid and esters were obtained. The compounds of phosphoric acid and esters can be used as a stabilizer including phosphate esters (A-2). Thereafter, 0.4 g of the compounds of phosphoric acid and esters were taken out to be dissolved in a solvent consisting of 75 g of distilled water and 25 g of isopropanol. The pH value was 2.42 when it was measured with a pH meter. In accordance with the above Formula I, Formula II, and Formula III, the respective contents of the phosphoric acid monoester, the phosphoric acid diester and phosphoric acid in the compounds of phosphoric acid and esters can be calculated, and the calculated results are shown in Table 1 below.

Comparative Example 1

The manufacturing procedures in Comparative Example 1 were substantially the same as the manufacturing procedures in Example 1 with the exception that chloroform was used instead of ethylene carbonate as the solvent for dispersing phosphorus pentoxide in Comparative Example 1. During the reaction, phosphorus pentoxide and BHET precipitated at the bottom of the reaction flask and did not disperse well in chloroform. At last, the products after the reaction were titrated with a 0.1 M aqueous potassium hydroxide solution. The results are shown in Table 1.

TABLE 1

|  | Phosphoric Acid Monoester (mol %) | Phosphoric Acid Diester (mol %) | Phosphoric Acid (mol %) |
|---|---|---|---|
| Example 1 | 79 | 10 | 11 |
| Example 2 | 42 | 38 | 20 |
| Comparative Example 1 | <1 | <1 | >99 |

According to the results shown in Table 1, the main compounds of phosphoric acid and esters in Example 1 and in Example 2 are composed of a phosphoric acid monoester and a phosphoric acid diester (between 80 mol % and 89 mol %). Specifically speaking, the content of the phosphoric acid monoester is between 42 mol % and 79 mol % and the content of the phosphoric acid diester is between 10 mol % and 38 mol % with the content of phosphoric acid all less than 20 mol %. In contrast, the main compounds of phosphoric acid and esters in Comparative Example 1 were composed of phosphoric acid with the phosphoric acid content higher than 99 mol % and with the phosphate esters content much lower than 1 mol %.

The above-mentioned compounds of phosphoric acid and esters can be used as the stabilizers in a polyester reaction to improve the heat resistance property of the polyester resin in a secondary processing stage. In order to make one of ordinary skills in the art comprehend the present invention better, the following paragraphs are provided to further describe the method for the preparation of the compounds of phosphoric acid and esters for use as a stabilizer in an esterification reaction and the tests for some physical properties.

Preparation Example 1

2161.5 g (13.021 moles) of terephthalic acid and 1009.1 g (16.276 moles) of ethylene glycol were added to a 5 liter reactor. Terephthalic acid was subjected to the esterification reaction with ethylene glycol at a temperature of 260° C. and under a nitrogen pressure of 2 Kg/cm². When the conversion rate of the esterification reaction is 80% or more, 300 ppm of antimony trioxide and the stabilizer including phosphate esters (A-1) which dispersed in ethylene glycol in advance were added to the reactor to obtain a mixture. The stabilizer including phosphate esters (A-1) has a theoretical phosphorus content of 15.8 ppm with respect to the polyester resin. The mixture was subjected to the polymerization reaction between 270° C. and 275° C. to obtain a polyester resin (B-1) including the compounds of phosphoric acid and esters.

The polyester resin (B-1) was treated at 225° C. for 1 hour, and the intrinsic viscosity (IV) and the color b values before and after the heat treatment were measured, and the measured results are shown in Table 2. The color b value is determined by the Hunter L, a, b scale for the determination of the appearance properties of a polyester resin. A larger color b value stands for a more yellowish appearance of a resin. A lower color b value stands for a better appearance of a resin with less yellowish appearance.

Preparation Example 2

The manufacturing procedures in Preparation Example 2 were substantially the same as the manufacturing procedures in Preparation Example 1, but the amount of the stabilizer including phosphate esters (A-1) in Preparation Example 2 was increased to 30 ppm (based on the theoretical phosphorus content of the stabilizer including phosphate esters (A-1) in the polyester resin) to obtain another polyester resin (B-2). Thereafter, the polyester resin (B-2) was treated at 225° C. for 1 hour. The IV values and the color b values before and after the heat treatment were measured. The corresponding manufacturing parameters and the measured results are shown in Table 2.

Control Example 1

The manufacturing procedures in Control Example 1 were substantially the same as the manufacturing procedures in Preparation Example 1, but no stabilizer including phosphate esters (A-1) was added in Control Example 1 to obtain another polyester resin (B-3). Thereafter, the polyester resin (B-3) was treated at 225° C. for 1 hour. The IV values and the color b values before and after the heat treatment were measured. The corresponding manufacturing parameters and the measured results are shown in Table 2.

Control Example 2

The manufacturing procedures in Control Example 2 were substantially the same as the manufacturing procedures in Preparation Example 1, but the stabilizer including phosphate esters (A-1) was replaced with phosphoric acid in Control Example 2 to obtain another polyester resin (B-4). Thereafter, the polyester resin (B-4) was treated at 225° C. for 1 hour. The IV values and the color b values before and after the heat treatment were measured. The corresponding manufacturing parameters and the measured results are shown in Table 2.

TABLE 2

| | | Preparation Example 1 | Preparation Example 2 | Control Example 1 | Control Example 2 |
|---|---|---|---|---|---|
| Acid | TPA (mole) | 13.021 | 13.021 | 13.021 | 13.021 |
| Alcohol | EG (mole) | 16.276 | 16.276 | 16.276 | 16.276 |
| stabilizer | type | phosphate ester (A-1) [*1] | phosphate ester (A-1) [*1] | N.A. | phosphoric acid |
| | amount (ppm) [*2] | 15.8 | 30 | 0 | 15.8 |
| Reaction time of polymerization (min) | | 240 | 250 | 215 | 240 |
| IV (dL/g) | before heat treatment | 0.613 | 0.605 | 0.673 | 0.609 |
| | after heat treatment | 0.519 | 0.489 | 0.497 | 0.463 |
| | Changes (%) | −15.3 | −19.1 | −26.1 | −23.9 |
| color b | before heat treatment | 2.9 | 2.4 | 8.2 | 2.3 |
| | after heat treatment | 1.7 | 2.0 | 8.5 | 3.9 |

[*1] The stabilizer including phosphate esters (A-1) corresponds to the compounds of phosphoric acid and esters which was prepared in Example 1.
[*2] Based on the phosphorus atom content to the total amount of the polyester resin.

From Table 2, in terms of the changes of the IV values before and after the heat treatment, the changes of the IV values in Preparation Example 1 and in Preparation Example 2 (for the examples with the addition of the stabilizer including phosphate esters (A-1)) are smaller than the changes of the IV values in Comparative Example 1 and in Comparative Example 2. The color b values of Preparation Example 1 and of Preparation Example 2 after the heat treatment still maintain lower values. In other words, compared with the polyester resins (B-3 and B-4) which were prepared in Control Example 1 and in Control Example 2, the polyester resins (B-1 and B-2) which were prepared in Preparation Example 1 and in Preparation Example 2 obviously show better heat resistance of secondary processing.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for preparing a stabilizer of phosphate ester, comprising the following steps:

(1) preparing a mixture comprising a phosphorus oxide compound, and a polar aprotic solvent, wherein there is no chemical reaction between the phosphorus oxide compound and the polar aprotic solvent and the polar aprotic solvent is a proton acceptor;

(2) adding bis(2-hydroxyethyl) terephthalate (BHET) into the mixture to perform a phosphorylation reaction to obtain a reaction mixture, wherein the bis(2-hydroxyethyl) terephthalate (BHET) has a melting point between 105° C. and 115° C.; and (3) hydrolyzing the reaction mixture to obtain a stabilizer of phosphate ester, wherein the stabilizer of phosphate ester comprises a phosphoric acid ester which is represented by the following formulas (I) and (II) and minor phosphoric acid and is free from a phosphoric acid triester:

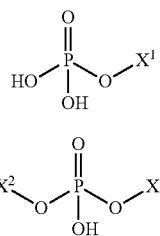

(I)

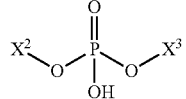

(II)

wherein $X^1$, $X^2$ and $X^3$ are independently selected from the moiety represented by the following formula (III):

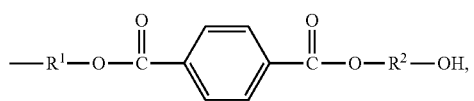

(III)

wherein $R^1$ and $R^2$ are independently selected from one of a linear alkylene group comprising 2 to 4 carbon atoms and a branched alkylene group comprising 3 to 4 carbon atoms in total.

2. The method for preparing a stabilizer of phosphate ester according to claim 1, wherein the phosphorus oxide compound is selected from phosphoric acid, polyphosphoric acid, phosphorus pentoxide and combinations thereof.

3. The method for preparing a stabilizer of phosphate ester according to claim 1, wherein the polar aprotic solvent is a cyclic carbonate.

4. The method for preparing a stabilizer of phosphate ester according to claim 3, wherein the polar aprotic solvent is selected from ethylene carbonate, propylene carbonate and combinations thereof.

5. The method for preparing a stabilizer of phosphate ester according to claim 1, wherein a reactant molar ratio of the phosphorus oxide compound and bis(2-hydroxyethyl) terephthalate is between 1:1 and 1:2.

6. The method for preparing a stabilizer of phosphate ester according to claim 1, wherein the phosphorylation reaction in the step (2) is to gradually heat the mixture to 80° C. and to keep a temperature of the mixture for 3 hours to perform the phosphorylation reaction.

7. The method for preparing a stabilizer of phosphate ester according to claim 1, wherein hydrolyzing the reaction mixture in the step (3) is to gradually cool off the reaction mixture to 70° C. and to keep a temperature of the reaction mixture for 1 hour to hydrolyze the reaction mixture.

8. The method for preparing a stabilizer of phosphate ester according to claim 1, wherein a molar ratio between the phosphate ester and the phosphoric acid in the stabilizer of phosphate ester is greater than 4.

9. The method for preparing a stabilizer of phosphate ester according to claim 8, wherein a content of the phosphoric acid in the stabilizer of phosphate ester is less than 20 mole %, based on a total amount of the stabilizer of phosphate ester as 100 mole %.

* * * * *